United States Patent
Sakuta

(10) Patent No.: US 6,984,390 B2
(45) Date of Patent: Jan. 10, 2006

(54) SILICONE COMPOUND AND COSMETIC PREPARATION

(75) Inventor: Koji Sakuta, Gunma (JP)

(73) Assignee: Shin-Etsu Chemical Co. Ltd., Tokyo (JP)

(*) Notice: Subject to any disclaimer, the term of this patent is extended or adjusted under 35 U.S.C. 154(b) by 137 days.

(21) Appl. No.: 10/297,064

(22) PCT Filed: May 25, 2001

(86) PCT No.: PCT/JP01/04422

§ 371 (c)(1),
(2), (4) Date: Dec. 2, 2002

(87) PCT Pub. No.: WO01/92376

PCT Pub. Date: Dec. 6, 2001

(65) Prior Publication Data

US 2003/0219395 A1    Nov. 27, 2003

(30) Foreign Application Priority Data

Jun. 1, 2000 (JP) .............................. 2000-164337

(51) Int. Cl.
*A61K 7/00* (2006.01)

(52) U.S. Cl. ............... 424/401; 424/70.12; 424/59; 514/63; 514/844; 556/400

(58) Field of Classification Search ............. 424/401, 424/70.12, 59, 489; 514/772.2, 844, 63; 556/400

See application file for complete search history.

(56) References Cited

U.S. PATENT DOCUMENTS 3,515,734 A    6/1970 Craig

FOREIGN PATENT DOCUMENTS

| | | |
|---|---|---|
| EP | 501791 | 9/1992 |
| EP | 523738 | 1/1993 |
| EP | 545002 | 6/1993 |
| JP | 4-145097 | 5/1992 |
| JP | 7-238009 | 9/1995 |
| JP | 7-278308 | 10/1995 |
| JP | 7-316024 | 12/1995 |
| JP | 10-203494 | * 2/2000 |
| JP | 2000-44432 | * 2/2000 |

OTHER PUBLICATIONS

Patent Abstracts of Japan, Mar. 18, 1991, vol. 15, No. 112; abstract of JP 03005488, Jan. 11, 1991.

* cited by examiner

*Primary Examiner*—Gary Kunz
*Assistant Examiner*—Konata M. George
(74) *Attorney, Agent, or Firm*—Millen White Zelano & Branigan, P.C.

(57) ABSTRACT

This invention provides a sterol-modified silicone compound which is low melting, hydrophilic and very suitable for emulsifying, represented by the general formula $R^1_a R^2_b SiO_{(4-a-b)/2}$, and having a melting point of 40° C. or less, and provides a cosmetic material containing this silicone compound having excellent stability and moisture retention properties $R^1$ in the general formula is a monofunctional alkyl group, aryl group, aralkyl group or fluorine-substituted alkyl group having 1–10 identical or different carbon atoms, which does not contain an aliphatic unsaturated bond, and $R^2$ is an organic group represented by the general formula $-(C_pH_{2p}O(C_qH_{2q}O)_r-X$, where X is a monofunctional residue excepting the hydroxyl group of sterol, a and b are integers satisfying the relations $1.0 \leq a \leq 2.5$, $0.001 \leq b \leq 1.0$, and $1.5 \leq a+b \leq 2.6$, respectively, p is an integer in the range 2–6, q is an integer in the range 2–4, and r is an integer in the range 3–200.

27 Claims, No Drawings

SILICONE COMPOUND AND COSMETIC PREPARATION

FIELD OF THE INVENTION

This invention relates to a low melting point, sterol-modified silicone compound, a cosmetic material containing this sterol-modified silicone compound, and a cosmetic material having excellent stability, moisture retention properties and adhesive properties which is easy to manufacture.

BACKGROUND OF THE INVENTION

Cosmetic materials are known which are blended with sterol compounds such as cholesterol and phytosterol in order to impart moistness to the skin or hair.

However, these sterol compounds are high melting point compounds as can be seen from the fact that the melting point of cholesterol is 149° C., and to use them as cosmetic material compositions, they must first be dissolved with heating or liquefied with a solvent before blending. If they are dissolved with heating, there is a problem that they cannot be blended with other components having poor heat stability. Also, when liquefying and blending, as they have a low solubility in solvents, only low concentration solutions could be prepared and only limited cosmetic material compositions could be obtained. Further, if crystallinity is high, crystals of sterol compounds separate and deposit during storage, so it is difficult to maintain storage stability.

It is known that crystallinity can be reduced by making the sterol compound react with a higher fatty acid to obtain a liquefied ester compound. However, when they contained such an ester compound, the cosmetic materials became sticky when applied to the skin, and it was difficult to obtain cosmetic materials having excellent organic functional characteristics.

To exploit the moistness of sterol compounds, it is desirable to make them into emulsions such as oil-in-water or water-in-oil, but as the sterol compound itself and the above-mentioned higher fatty acid ester had low hydrophilic properties, an activator had to be used to make the emulsion composition, and a decline of organic functionality due to this activator could not be avoided.

It is also known that adding ethylene oxide to a sterol compound reduces crystallinity, imparts hydrophilic properties and leads to an emulsion-type compound. However, the stickiness on the skin could not be eliminated.

To improve organic functionality, a sterol-modified silicone compound has also been developed (Japanese Patent Application Public Disclosure No. Hei 4-145097, Koho), but a satisfactory cosmetic material could still not be obtained.

The Inventors carried out intensive studies in order to solve the above-mentioned problems. They then discovered a sterol-modified silicone compound having low crystallinity, no stickiness on the skin, excellent organic functionality and hydrophilic properties.

It is therefore a first object of this invention to provide a sterol-modified silicone compound suitable for an emulsion composition having a low melting point, and hydrophilic properties.

It is a second object of this invention to provide a cosmetic material having excellent stability and moistness.

DISCLOSURE OF THE INVENTION

This invention is a silicone compound represented by the general formula $R^1_a R^2_b SiO_{(4-a-b)/2}$, and having a melting point of 40° C. or less, and a cosmetic material containing this compound.

$R^1$ in the above-mentioned general formula is a monofunctional alkyl group, aryl group, aralkyl group or fluorine-substituted alkyl group having 1–10 identical or different carbon atoms, which does not contain an aliphatic unsaturated bond, and $R^2$ is an organic group represented by the general formula $-(C_pH_{2p})O(C_qH_{2q}O)_r-X$, where X is a monofunctional residue excepting the hydroxyl group of sterol. a and b are integers satisfying the relations $1.0 \leq a \leq 2.5$, $0.001 \leq b \leq 1.0$, and $1.5 \leq a+b \leq 2.6$, respectively, p is an integer in the range 2–6, q is an integer in the range 2–4, and r is an integer in the range 3–200.

By blending the silicone compound of this invention, a cosmetic material is obtained having excellent skin contact, no stickiness and excellent feel. The product is easily manufactured Also, a cosmetic material can be provided which exhibits no change with temperature or time, and which is very stable.

DESCRIPTION OF THE PREFERRED EMBODIMENTS

This invention will now be described in further detail.

$R^1$ in the average empirical formula $R^1_a R^2_b SiO_{(4-a-b)/2}$ is a monofunctional alkyl group, aryl group, aralkyl group or fluorine-substituted alkyl group having 1–10 identical or different carbon atoms, which does not contain an aliphatic unsaturated bond.

$R^2$ is an organic group represented by the general formula $-(C_pH_{2p})O(C_qH_{2q}O)_r-X$, where X is a monofunctional residue excepting the hydroxyl group of sterol. a and b are integers satisfying the relations $1.0 \leq a \leq 2.5$, $0.001 \leq b \leq 1.0$, and $1.5 \leq a+b \leq 2.6$, respectively, p is an integer in the range 2–6, q is an integer in the range 2–4, and r is an integer in the range 3–200.

$R^1$ may be an alkyl group, such as methyl, ethyl, propyl, butyl, pentyl, hexyl, heptyl, octyl, nonyl or decyl; a saturated cycloaliphatic hydrocarbon group, such as cyclopentyl or cyclohexyl, an aryl group, such as phenyl or tolyl, or a fluorine-substituted alkyl group, such tridfluoropropyl, nonafluorohexyl or heptadecyl fluorodecyl. It is particularly preferred that methyl accounts for 50 mole % or more.

The silicone compound of this invention may be obtained by reacting at least one type of alkylene oxide selected from ethylene oxide, propylene oxide, butylene oxide and tetrahydrofuran, with a hydroxyl group-containing sterol compound.

The intermediate obtained by chain termination of the end with an alkenyl ether is then made to undergo an addition reaction with a Si—H containing organohydrogen polysiloxane.

In the sterol compound of the starting material, it is preferred that its hydroxyl group is in the third, sixteenth or seventeenth position, but particularly preferred that it is in the third position, of the steroid skeleton. Specific examples of suitable sterol compounds are cholesterol, ergosterol, lanosterol, phytosterol and estradiol.

In view of availability as an oil for cosmetic materials and productivity, cholesterol is particularly preferred.

a is 1.0–2.5, but preferably 1.2–2.2, and b is 0.001–1.0, but preferably 0.005–0.5. a+b is 1.5–2.6, but preferably 1.8–2.2. If a is less than 1.0, the siloxane content decreases and the crystallinity reducing effect decreases, whereas if it is more than 2.5, the sterol group content decreases and skin contact decreases. If b is less than 0.001, the sterol group content decreases and skin contact is reduced, whereas if it is larger than 1.0, the siloxane content decreases and the crystallinity reducing effect decreases. p is an integer in the range 2–6, but preferably 3 or 4, q is an integer in the range 2–4, but preferably 2 or 3, and r is an integer in the range 3–200, but preferably 5–100.

The cosmetic material of this invention contains the aforesaid sterol-modified silicone compound as an essential component, and preferably contains 0.1–70.0 wt % of this sterol-modified silicone compound as component (a). An improved cosmetic material can be obtained by including at least one of a phospholipid, a compound having an alcoholic hydroxyl group in the molecular structure, an oil, water, powder, colorant, surfactant, crosslinked organopolysiloxane, silicone resin and ultraviolet screening component as component (b).

The amount of the silicone compound (a) of this invention which is contained in the cosmetic material of this invention is preferably 0.1–70.0 wt %, but more preferably 1.0–50.0 wt %, as described above. When it is less than 0.1 wt %, it becomes difficult to impart moistness to the cosmetic material which uses it, and when it is more than 70.0 wt %, the cosmetic material becomes sticky.

The phospholipid (b-1) which is one of the components of the aforesaid (b) of this invention, may be phosphatidyl choline, phosphatidyl ethanolamine, phosphatidyl serine, phosphatidyl glycerol, phosphatidyl inositol or a phosphine choline lipid. It may also be a compound similar to these or a composition containing them such as soybean lecithin, egg yolk lecithin, or hydrogen addition products thereof. These phospholipids may be used independently, or two or more may be used together.

The compound (b-2) having an alcoholic hydroxyl group in its molecular structure, which is one of the components of (b) of this invention, may be one of the following.

Examples of alcohols are lower alcohols such as ethanol, propanol and isopropanol, polyhydric alcohols such as ethylene glycol, propylene glycol, 1,3-butylene glycol, glycerol and diglycerol, alcohols such as ethylene glycol mono alkyl ether and diethylene glycol monoethyl ether, sugar alcohols such as sorbitol and maltose, and cholesterol, sitosterol, phytosterol and lanosterol.

Examples of water-soluble polymers include vegetable polymers, such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer;

polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride.

In these polymers, film-forming agents, such as polyvinyl alcohol and polyvinyl pyrrolidine, are also included.

These compounds comprising an alcoholic hydroxyl group in the molecular structure may be used alone, or two or more may be used in conjunction as necessary. The amount of the compound (b-2) comprising an alcoholic hydroxyl group in the molecular structure differs depending on the form of the cosmetic material, but is preferably 0.1–70.0 wt % and more preferably 1.0–50.0 wt %.

When it is less than 0.1 wt %, moisture retention, antimicrobial properties and antiseptic properties are inadequate, and when it is more than 70.0 wt %, stickiness increases which is undesirable for cosmetic materials.

The oil (b-3) which may be used as one of the components of (b) of this invention may be a natural animal or vegetable fat or oil, or a semi-synthetic fat or oil. Examples include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, methyl caster oil fatty acid, sunflower oil, grape seed oil, bayberry wax, jojoba oil, macadamia nut oil, beeswax, mink oil, cottonseed oil, cotton wax, Japan wax, haze kernel oil, montan wax, coconut oil, hydrogenated coconut oil, triconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether (POE is polyoxyethylene, hereafter idem), POE lanolin alcohol acetate, polyethylene glycol lanolin fatty acid, POE hydrogenated lanolin alcohol ether, and egg yolk oil.

Examples of hydrocarbon oils include ozokerite, squalane, squalene, ceresine, paraffin, paraffin wax, liquid paraffin, pristane, polyisobutylene, microcrystalline wax and vaseline; and examples of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oils include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, -2-hexyldecyl myristate, myristyl myristate, hexyldecyl dimethylocanoate, ethyl laurate, hexyl laurate, N-lauroyl-L-glutaminic acid 2-octyldodecyl ester, diisostearyl malic acid, dextrin palmitic acid ester, dextrin stearic acid ester, dextrin 2-ethylhexanoic acid palmitic acid ester, cane sugar palmitic acid ester, cane sugar stearic acid ester, monobenzylidene sorbitol and dibenzylidene sorbitol.

Examples of glyceride oils include acetoglyceride, tri-isooctanoic acid glyceride, triisostearic acid glyceride, tri-isopalmitic acid glyceride, monostearic acid glyceride, di-2-heptylundecanoic acid glyceride and trimyristic acid glyceride.

Examples of silicone oils are organopolysiloxanes having from low to high viscosities, such as dimethylpolysiloxane, methylphenylpolysiloxane, methylhydrogenpolysiloxane and dimethylsiloxane-methylphenylsiloxane copolymer; cyclic siloxanes, such as octamethylcyclotetrasiloxane, decamethylcyclopentasiloxane, dodecamethyleyclohexasiloxane, tetramethyltetrahydrogencyclotetrasiloxane and tetramethyltetraphenylcyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, amino-modified silicones, fluorine-modified silicones and solid silicones.

Examples of fluorine-containing oils are perfluoropolyether, perfluorodecalin, perfluorooctane, fluorinated pitch and fluoroalcohols.

There is no particular limitation on the structure of these silicone oils which may be straight-chain, branched or cyclic, but it is particularly preferred that they essentially comprise a —[Si—O]n— skeleton. In this case, part of the molecule may contain a 13 Si—$(CH_2CH_2)_m$—Si— bond.

These oils may be used alone, or two or more may be used in conjunction as necessary.

The amount of these oils depends on the form of the cosmetic material, but it is normally 0.1–50.0 wt % and preferably 1.0–30 wt %. If it is less than 0.1 wt %, the oil may not have any effect, whereas if it is more than 50.0 wt %, the full effect of the sterol-modified silicon compound of this invention will not be realized.

In this invention, the cosmetic material may further comprise water, (b-4), as one component thereof if necessary. The water content is 0.1–90.0 wt %, and may be increased or decreased as necessary according to the form of cosmetic material.

An excellent cosmetic material according to the present invention can be obtained using only components (a) and (b-1)–(b-4), but the following components (b-5), (b-6), (b-7), (b-8), (b-9) may also be added as necessary.

The component (b-5) in the above is a powder and/or colorant such as described below. Such powders are not particularly restricted as to their shapes (whether they are spherical, rod-shaped, acicular, plate-shaped, amorphous, scale-like or spindle-shaped), their particle sizes (whether they are of the order of fume, fine grain or pigment), and their structures (whether they are porous or nonporous), provided that they have so far been used in traditional cosmetic materials. For instance, inorganic powders, organic powders, surfactant metal salt powders, colored pigments, pearl pigments, metallic powder pigments and natural colors can be added to the present cosmetic materials, if desired.

Examples of usable inorganic powders include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxide, boron nitride and silica.

Examples of usable organic powders include resin powders, such as polyamide powder, polyester powder, polyethylene powder, polypropylene powder, polystyrene powder, polyurethane powder, benzoguanamine powder, polymethyl benzoguanamine powder, poly(tetrafluoroethylene) powder, polymethyl methacrylate powder, cellulose powder, silk powder, nylon powder (e.g., 12-nylon powder or 6-nylon powder), silicone elastomer powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder and polycarbonate resin powder; microcrystalline fiber powder; starch powder; and lauroyl lysine powder. According to this invention, powders having a silicone resin or silicone elastomer as their skeleton, and powders comprising a —[Si—O]$_n$— repeating unit in their molecular skeleton, are particularly preferred. In this case, part of the molecule may contain a —Si—$(CH_2CH_2)_m$—Si— bond.

Examples of usable surfactant metal salt powders (metal soap powders) include powders of zinc stearate, aluminum stearate, calcium stearate, magnesium stearate, zinc myristate, magnesium myristate, zinc cetylphosphate, calcium cetylphosphate and zinc sodium cetylphosphate.

Examples of usable colored pigments include inorganic red pigments, such as iron oxide, iron hydroxide and iron titanate; inorganic brown pigments, such as γ-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments as recited above.

Examples of usable pearl pigments include taitanium dioxide-coated mica, bismuth oxychloride, taitanium dioxide-coated bismuth oxychloride, taitanium dioxide-coated talc, fish scales, and taitanium dioxide-coated colored mica; and examples of a usable metallic powder pigment include aluminum powder, copper powder and stainless powder.

Examples of tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207);

and the natural pigments described above include powders of carminic acid, laccaic acid, carthamin, bradilin and crocin.

To the extent that it does not interfere with the effect of this invention, these powders may be treated with ordinary oils, silicone oils, fluorine compounds or surfactants. For example, the surface may first be treated with a fluorine compound, silicone resin, pendant, silane coupling agent, titanium coupling agent, oil, N-acylated lysine, polyacrylic acid, metal soap, aminoacid, inorganic compound, plasma treatment or mechanochemical treatment. Of these, the use of a silicone elastomer spherical powder, polyethylene powder, polypropylene powder, polytetrafluoroethylene powder, silicone rubber powder or polyurethane powder gives a product with enhanced stability over time and feel.

These powders may be used alone, or two or more may be used in conjunction. The blending proportion of the powder depends on the form of the cosmetic material, but it is 0.1–50 wt % and preferably 0.5–30 wt % relative to the total amount of cosmetic material. According to this invention, at least part of these powders may be substituted by the aforesaid colorants.

The component (b-6) is one of the surfactants shown below. The surfactant used in this invention may be anionic, cationic, non-ionic or amphoteric, there being no particular limitation, and any surfactant may be used provided that it is used in ordinary cosmetic materials. Specific examples are given below.

Examples of usable anionic surfactants include fatty acid soaps, such as sodium stearate or triethanolamine palmitate; alkyl ether carboxylic acids and salts thereof; salts of amino acid-fatty acid condensates; alkanesulfonates; alkenesulfonates; sulfonated fatty acid esters; sulfonated fatty acid amides; sulfonates of formaldehyde condensate type; alkylsulfates; higher secondary alcohol sulfates; alkyl and aryl ether sulfates; fatty acid ether sulfates, fatty acid alkylolamide sulfates; ether sulfates, such as Turkey red oil; alkyl phosphates; ether phosphates; alkyl aryl ether phosphates; amide phosphates; and N-acylaminoacid activators.

Examples of usable cationic surfactants include amine salts, such as alkylamine salts, polyamines and aminoalcohol fatty acid derivatives, quaternary alkylammonium salts, quaternary arylammonium salts, pyridinium salts and imidazolium salts.

Examples of usable nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopoly-siloxanes, organopolysiloxanes modified with both polyoxyalkylene and alkyl groups, alkanolamides, sugar ethers and sugar amides.

Examples of usable amphoteric surfactants include betaine, aminocarboxylic acid salts and imidazoline derivatives. The blending proportion of the surfactant is preferably 0. 1–20 wt %, but more preferably 0.5–10 wt %, relative to the total amount of cosmetic material.

The component (b-7) is a crosslinked organopolysiloxane. Crosslinked organopolysiloxanes suitable for addition to the present cosmetic material are those which cause swelling when they contain a silicone having a low viscosity of from 0.65–10.0 mm$^2$/s (25° C.) in an amount larger than the weight of the crosslinked organopolysiloxanes themselves. It is preferable that the cross-linked structure of those organopolysiloxanes be formed by reaction between hydrogen atoms bonded directly to silicon atoms and a crosslinking agent having, on average, at least 1.5 vinylic reactive moieties per molecule. In the cross-linking reaction, it is appropriate to use a cross-linking agent containing at least one moiety selected from polyoxyalkylene, alkyl, alkenyl, aryl or fluoroalkyl moieties. The blending proportion of such cross-linked organopolysiloxanes in the present cosmetic material is from 0.1 to 30.0 wt %, but preferably from 1.0 to 10.0 wt %, of the total weight of the cosmetic material.

The component (b-8) is a silicone resin such as an acryl-silicone graft or block copolymer or a silicone compound having a reticular structure, but acrylsilicone resins are particularly suitable for the present cosmetic materials. Further, it is desirable that at least one moiety selected from a group consisting of pyrrolidone, long-chain alkyl, polyoxyalkylene and fluoroalkyl moieties be present in such a silicone resin. Further, it is appropriate for those silicone resins to be reticular silicone compounds. When the silicone resins, such as acryl-silicone graft or block copolymer and silicone compounds having a reticular structure, are blended in the present cosmetic material, the appropriate proportion of silicone resins is from 0.1–20 wt %, but preferably from 1–10 wt %, of the total weight of the cosmetic material.

The component (b-9) is an ultraviolet defense component, which in addition to an ultraviolet dispersing agent such as the inorganic pigments and metal powders mentioned above, may also be an organic ultraviolet absorption agent. Specific examples are benzoic acid ester absorption agents such as p-aminobenzoic acid, ethyl p-aminobenzoic acid, glyceryl p-aminobenzoic acid, amyl p-dimethylaminobenzoic acid, octyl p-dimethylaminobenzoic acid and ethyl 4-[N,N-di(2-hydroxypropyl)aminobenzoic acid; salicylic acid ultraviolet absorption agents such as methyl salicylate, ethylene glycol salicylate, phenyl salicylate, octyl salicylate, benzyl salicylate, p-tert-butylphenyl salicylate and homomenthyl; silicic acid ultraviolet absorption agents such as benzyl salicylate, 2-ethoxyethyl p-methoxysilicic acid, octyl p-methoxysilicic acid and glyceryl di-p-methoxysilicic acid mono-2-ethylhexanoic acid; urocanic acid ultraviolet absorption agents such as urocanic acid and ethyl urocanate; benzophenone ultraviolet absorption agents such as hydroxymethoxybenzophenone, hydroxymethoxybenzophenone sulfonic acid, sodium, hydroxymethoxybenzophenone sulfonate, dihydroxymethoxybenzophenone, sodium dihydroxydimethoxybenzophenone sulfonate, 2,4-dihydroxybenzophenone and tetrahydroxybenzophenone; dibenzoylmethane ultraviolet absorption agents such as 4-tert-butyl-4'-methoxy-dibenzoylmethane; anthranyl ultraviolet absorption agents such as menthyl anthranilic acid; and benzotriazole derivatives such as 2-(2-hydroxy-5-methylphenyl)benzotriazole. In addition, polymer derivatives, silane or siloxane derivatives thereof may also be mentioned.

The blending proportion of these ultraviolet absorption agents is preferably 0.1–20.0 wt %, but more preferably 1.0–10.0 wt % relative to the total amount of cosmetic material. Of these organic ultraviolet absorption agents, 2-ethylhexyl p-methoxysilicic acid and 4-t-butyl-4'-methoxy-dibenzoylmethane are particularly preferred.

These organic ultraviolet absorption agents may also be sealed in a polymer powder. In this case, the polymer powder may be balloon It is preferred that the average first order particle diameter of the polymer powder is within the range 0.1–50 micrometers, and its particle size distribution may be broad or sharp. Examples of polymer types are acrylic resin, methacrylic resin, styrene resin, urethane resin, polyurethane resin, polypropylene resin, polyethylene terephthalate resin, silicone resin, nylon resin and acrylamide resin. It is preferred that the organic ultraviolet absorption agent is incorporated in these polymer powders to the extent of 0.1–30.0 wt % of these polymer powders, and particularly preferred that 4-t-butyl-4'-methoxy-dibenzoyl-methane is blended.

The agents used in general cosmetic materials, such as film-forming agents, oil-soluble gelling agents, clay minerals modified with organic compounds, resins, ultraviolet absorbents, moisture retention agents, antiseptics, antimicrobial agents, perfumes, salts, antioxidants, pH regulators, chelating agents, refrigerants, anti-inflammatory agents, skin beautifying components (skin whiteners, cell activators, rough, dry skin improvers, blood circulation promoters, skin astringents and anti-seborrheic agents), vitamins, amino acids, nucleic acids, hormones and clathrate compounds, can be added so far as they have no adverse influence on the effects of the present invention.

Examples of oil-soluble gelling agents which can be added include metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay. These oil-soluble gelling agents may be used alone or in conjunction, as necessary.

Examples of moisture retention agents which can be added include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylate, polyoxyethylene glycoside, and polyoxypropylene methylglycoside.

Examples of antiseptic agents which can be added include alkyl p-hydroxybenzoates, benzoic acid, sodium benzoate, sorbic acid, potassium sorbate and phenoxyethanol; and examples of antimicrobial agents which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitizers and phenoxyethanol.

Examples of antioxidants which can be added include tocopherol, butylhydroxyanisole, dibutylhydroxytoluene and phytic acid; examples of pH regulators which can be added include lactic acid, citric acid, glycolic acid, succinic acid, tartaric acid, dl-malic acid, potassium carbonate, sodium hydrogen carbonate and ammonium hydrogen carbonate; examples of chelating agents which can be added include alanine, sodium ethylenediaminetetraacetate, sodium polyphosphate, sodium metaphosphate and phosphoric acid; examples of refrigerants which can be added include L-menthol and camphor; and examples of anti-inflammatory agents which can added include allantoin, glycyrrhizin and salts thereof, glycyrrhetinic acid and stearyl glycyrrhetinate, tranexamic acid and azulene.

Examples of skin-beautifying components which can be added include whitening agents, such as placenta extract, arbutin, glutathione and Yukinoshita extract; cell activators, such as royal jelly, photosensitizers, cholesterol derivatives and calf blood extract; rough dry skin improvers; blood circulation improvers, such as nonylic acid vanillyl amide, benzyl nicotinate, $\beta$-butoxyethyl nicotinate, capsaicin, zingerone, cantharis tincture, ichtammol, caffeine, tannic acid, $\alpha$-borneol, tocopheryl nicotinate, inositol hexanicotinate, cyclandelate, cinnarizine, tolazoline, acetyl choline, verapamil, cepharanthin and $\gamma$-oryzanol; skin astringents, such as zinc oxide and tannic acid; and anti-seborrheic agents, such as sulfur and thianthol.

Examples of vitamins which can be added include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as $\alpha$-tocopherol, $\beta$-tocopherol, $\gamma$-tocopherol, dl-$\alpha$-tocopheryl acetate, dl-$\alpha$-tocopheryl nicotinate and dl-$\alpha$-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of aminoacids which can be added include glycine, valine, leucine, isoleucine, serine, threonine, phenylaranine, alginine, lysine, aspartic acid, glutamic acid, cystine, cysteine, methionine, and tryptophan; examples of nucleic acids which can be added include deoxyribonucleic acid; and examples of hormones which can be added include estradiol and ethenyl estradiol.

Examples of astringents which can be added are aluminum chlorohydrate and aluminum-zirconium chlorohydrate, specific examples being Microdry UF, REACH 101, REACH 103, REACH 301, REACH 301 solution, REACH 501, REACH 501 solution, REHYDOL II, REACH AZP 902, REACH 908, REACH 855, REACH AZZ 902, REACH 855, REACH AZN 885, REZAL 36P, REACH 36 SOLUTION, REACH 36GP, REACH 36G solution and REACH 67P, REACH 67 solution (all products of REHEIS Co. Ltd.).

There is no particular limitation on the uses of the cosmetic material of the present invention, suitable examples being skin care products, hair treatment products, antiperspirants, make-up materials, ultraviolet defense products and perfume solvents. This includes basic products such as emulsions, creams, lotions, calamine lotion, sunscreens, suntan lotions, after shave lotion, preshave lotion, packs, cleansers, face soap, anti-acne cosmetic materials and essences, make-up materials such as foundations, rouge, eye shadow, eye blow, cheek, lipstick and nail color, and shampoo, rinse, conditioner, hair colouring agents, hair tonic, setting agents, body powder, bath aids, hand soaps and perfumes. There is no particular limitation on the form of the product which may be a liquid, emulsion, cream, solid, paste, gel, powder, laminate, mousse or spray.

EXAMPLES

The present invention will now be illustrated in greater detail by reference to the following examples. However, the invention should not be construed as being limited to these examples. The term "%" used hereinafter means "% by weight" unless otherwise noted.

Example 1

200 weight parts of an organohydrogen siloxane represented by the following average empirical formula (1):

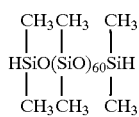

(1)

and 98 weight parts of a cholesterol derivative represented by the following average empirical formula (2) (here, the organic group A represents a cholesterol residue), $$CH_2=CHCH_2O(C_2H_4O)_7(C_3H_6O)_3—A \quad (2)$$

were placed in a reaction vessel, and mixed with 90 weight parts of ethanol. 0.1 weight parts of a 2 wt % toluene solution of chloroplatinic acid was added, and a reaction performed under reflux of solvent for 5 hours. The reaction mixture was heated under reduced pressure to distill off the solvent, and filtered to obtain the compound represented by the following average empirical formula.

This compound was light yellow, transparent, and it had a viscosity of 1200 mm²/s at 25° C.

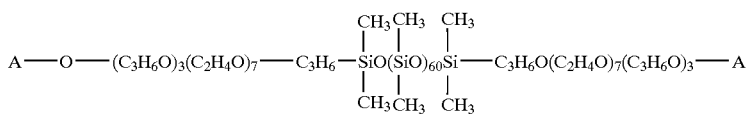

Example 2

200 weight parts of an organohydrogen siloxane represented by the following average empirical formula (3),

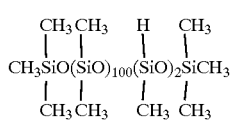

(3)

65 weight parts of the cholesterol derivative represented by the average empirical formula (2) used in Example 1, and 80 weight parts of 2-propanol, were mixed in a reaction vessel, 0.1 weight parts of a 2 wt % toluene solution of chloroplatinic acid was added, and a reaction performed under reflux of solvent for 5 hours. The reaction mixture was heated under reduced pressure to distill off the solvent, and filtered to obtain the compound represented by the following average empirical formula.

This compound was light yellow, transparent, and it had a viscosity of 2200 mm²/s at 25° C.

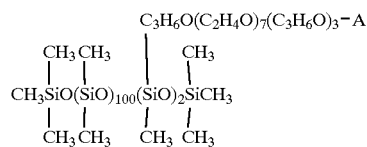

Example 3

100 weight parts of an organohydrogen siloxane represented by the following average empirical formula (4),

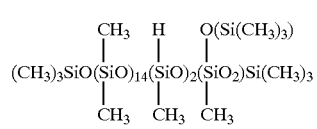

(4)

and 150 weight parts of a phytosterol derivative represented by the following average empirical formula (5) (here, the organic group B represents a phytosterol residue), $$CH_2=C(CH_3)CH_2O(C_2H_4O)_{10}—B \quad (5)$$

were placed in a reaction vessel, and mixed with 80 weight parts of 2-propanol. 0.1 weight parts of a 2 wt % ethanol solution of chloroplatinic acid was added, and a reaction performed under reflux of solvent for 5 hours. The reaction

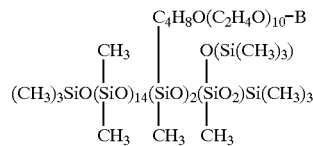

mixture was heated under reduced pressure to distill off the solvent, and filtered to obtain the compound represented by the following average empirical formula.

This compound was a light yellow solid, and it had a melting point of 30° C.

Example 4

25 weight parts of an organohydrogen siloxane represented by the following average empirical formula (6) and 110 weight parts of a cholesterol derivative represented by the following average empirical formula (7) (here, the organic group A represents a cholesterol residue),

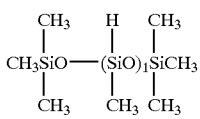

(6)

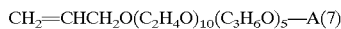

$CH_2=CHCH_2O(C_2H_4O)_{10}(C_3H_6O)_5-A$ (7)

were placed in a reaction vessel, and mixed with 50 weight parts of 2-propanol. 0.1 weight parts of a 2 wt % toluene solution of chloroplatinic acid was added, and a reaction performed under reflux of solvent for 5 hours. The reaction mixture was heated under reduced pressure to distill off the solvent, and filtered to obtain the compound represented by the following average empirical formula:

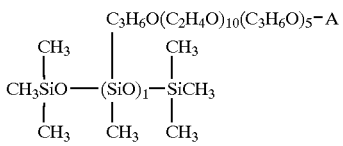

This compound was light yellow, transparent, and it had a viscosity of 590 $mm^2/s$ at 25° C.

Next, various cosmetic materials were prepared using the compounds obtained in Examples 1–4, and were evaluated according to the following methods.

Functionality Tests

The functionality of experimental products was evaluated by a panel of 10 experts.

If the functional characteristic was excellent, the product received +5 points, if it was poor it received 0 points, and the intermediate region was divided into four levels. The test results were expressed as a total number of points for all panelists. Therefore, the result is better the higher the number of points.

Examples 5, 6 and Comparative Examples 1, 2

A cosmetic water was obtained according to the following procedure. The blending amount is expressed in wt %.

|  | Example 5 | Example 6 | Comparative Example 1 | Comparative Example 2 |
|---|---|---|---|---|
| 1,3-butylene glycol | 8.0 | 0 | 8.0 | 0 |
| Dipropylene lycol | 0 | 8.0 | 0 | 8.0 |
| Lecithin | 0.1 | 0.1 | 0.1 | 0.1 |
| Silicone compound of Example 1 | 2.0 | 0 | 0 | 0 |
| Silicone compound of Example 2 | 0 | 2.0 | 0 | 0 |
| Cholesterol derivative[1] | 0 | 0 | 2.0 | 0 |
| Cholesterol derivative[2] | 0 | 0 | 0 | 2.0 |
| Purified water | 89.9 | 89.9 | 89.9 | 89.9 |

[1]$HO(C_2H_4O)_{10}$-A (A is a cholesterol residue)
[2]Cholesteryl 2-ethylhexanoate The test results are shown below, and it can be seen that in the Examples according to this invention, as compared to the Comparative Examples, the product is highly transparent and has an excellent storage stability. It has a clean feel when applied to the skin, and has good contact properties therewith.

|  | Appearance | Storage stability (room temperature, after 30 days) | Clean feel | Skin contact |
|---|---|---|---|---|
| Example 5 | Translucent | Translucent, no deposit | 42 | 39 |
| Example 6 | Translucent | Translucent, no deposit | 44 | 40 |
| Comparative Example 1 | Slightly opaque | Slightly opaque, with deposit | 25 | 16 |
| Comparative Example 2 | Slightly opaque | Slightly opaque, with deposit | 29 | 22 |

Example 7 and Comparative Examples 3, 4

A lipstick was obtained according to the following procedure. The blending amount is expressed in wt %.

|  | Example 7 | Comparative Example 3 | Comparative Example 4 |
|---|---|---|---|
| Candellila wax | 8.0 | 8.0 | 8.0 |
| Polyethylene wax | 8.0 | 8.0 | 8.0 |
| Silicone compound of Example 3 | 15.0 | 0 | 0 |
| Pentaerythrytol fatty acid derivative | 0 | 15.0 | 0 |
| Abietic acid methyl ester | 0 | 0 | 15.0 |
| Methylphenyl silicone[3] | 3.0 | 3.0 | 3.0 |
| Isotridecyl isononanoate | 20.0 | 20.0 | 20.0 |
| Glyceryl isostearate | 16.0 | 16.0 | 16.0 |
| Polyglyceryl triisostearate | 28.8 | 28.8 | 28.8 |
| Pigment | 0.2 | 0.2 | 0.2 |

The needle penetration load was measured by a rheometer, and the hardness change of the lipstick was examined. These results and functional test results are shown in the -following table. The functional tests were performed according to the following method.

As a result, effectively identical results were obtained at 5° C. and 20° C., but at 40° C., the product according to the present invention showed a load value of approximately 1.5 times than that of the comparative examples. In other words, a lipstick can be obtained which does not easily harden at low temperature, and does not easily soften at high temperature. It also spreads very well on the lips and has an excellent contact therewith.

Example 8

Suntan Cream

|  | Needle Penetration Load (g) | | | Functional tests | |
|---|---|---|---|---|---|
|  | 5° C. | 20° C. | 40° C. | Elongation | Contact |
| Example 7 | 105.0 | 69.5 | 30.0 | 41 | 43 |
| Comparative Example 3 | 116.5 | 67.0 | 21.0 | 20 | 19 |

-continued

|  | Needle Penetration Load (g) | | | Functional tests | |
|---|---|---|---|---|---|
|  | 5° C. | 20° C. | 40° C. | Elongation | Contact |
| Comparative Example 4 | 96.5 | 62.0 | 20.0 | 22 | 23 |

| (Component) | % |
|---|---|
| 1. Silicone compound of example 4 | 15.0 |
| 2. Dimethylpolysiloxane (100 cs) | 5.0 |
| 3. Silicone wax | 0.5 |
| 4. Polyether oleyl co-modified silicone* | 6.0 |
| 5. Palmitic acid | 0.2 |
| 6. Dimethyloctyl p-aminobenzoic acid | 0.5 |
| 7. 4-t-butyl-4'-methoxydibenzoylmethane | 0.5 |
| 8. Kaolin | 0.5 |
| 9. Red ocher | 0.2 |
| 10. Yellow iron oxide | 0.3 |
| 11. Black iron oxide | 0.1 |
| 12. Titanium oxide-coated mica | 1.0 |
| 13. L-sodium glutamate | 3.0 |
| 14. 1,3-butylene glycol | 5.0 |
| 15. Dioctadecyldimethylammonium chloride | 0.1 |
| 16. Antioxidant | Suitable amount |
| 17. Preservative | Suitable amount |
| 18. Perfume | Suitable amount |
| 19. Purified water | Remainder |

*KF-6026 (Shin-Etsu Chemical Co., Ltd.)

(Manufacturing Method)

A: Components 1–7, 16 and 17 were dissolved with heating.

B: Component 15, and part of 19 were stirred with heating, and Components 8–12 were added and dispersed.

C: Components 13–14 and the remainder of 19 were dissolved homogenously, and were mixed with B.

D: C was gradually added to A with stirring to emulsify it, cooled, and Component 18 was added. A suntan cream was thereby obtained.

The suntan cream obtained above had a fine texture and spread lightly. It was non-sticky, non-oily, and moist, fresh and pleasant to use. It was highly suited to the skin and lasted well. It showed no change with temperature or time, did not separate, did not become lumpy, and was very stable.

Example 9

Foundation

| (Component) | (%) |
|---|---|
| 1. Compound of Example 1 | 45.0 |
| 2. Dimethylpolysiloxane (6 cs) | 5.0 |
| 3. Polyether-modified siloxane* | 1.5 |
| 4. Polyether oleyl co-modified siloxane** | 0.5 |
| 5. Octadecyl dimethylbenzyl ammonium salt-modified montmorillonite | 4.0 |
| 6. Hydrophobically-treated titania*** | 10.0 |
| 7. Hydrophobically-treated talc*** | 6.0 |
| 8. Hydrophobically-treated mica*** | 6.0 |
| 9. Hydrophobically-treated red ocher*** | 1.6 |
| 10. Hydrophobically-treated yellow iron oxide*** | 0.7 |
| 11. Hydrophobically-treated black iron oxide*** | 0.2 |
| 12. Dipropylene glycol | 5.0 |

-continued

| (Component) | (%) |
|---|---|
| 13. P-oxybenzoic acid methyl ester | 0.3 |
| 14. 2-amino-2-methyl-1,3-propanediol | 0.2 |
| 15. Hydrochloric acid | 0.1 |
| 16. Perfume | Suitable amount |
| 17. Water | Remainder |

*KF-6017 (Shin-Etsu Chemical Co., Ltd.)
**KF-6026 (Shin-Etsu Chemical Co., Ltd.)
***Hydrophobic treatment: 2% methylhydrogenpolysiloxane was added to the powder, and then heat-treated.

(Manufacturing Method)

A: Components 1–5 are mixed with heating, Components 6–11 were added, and blended homogeneously.

B: Components 12–15 and 17 were dissolved with heating (pH of aqueous system, 9.0)

C: B was gradually added to A with stirring, emulsified, cooled, and Component 16 was added. A foundation was thereby obtained.

The foundation obtained above had a fine texture and spread lightly. It was non-sticky, non-oily, and moist, fresh and pleasant to use. It lasted well, showed no change with temperature or time, and was very stable.

Example 10

Hair Cream

| (Component) | (%) |
|---|---|
| 1. Compound of Example 2 | 10.0 |
| 2. Methylphenyl polysiloxane | 5.0 |
| 3. Squalane | 4.0 |
| 4. Silicone resin | 1.0 |
| 5. Dioleic acid glyceryl | 2.0 |
| 6. Polyether oleyl co-modified silicone* | 4.0 |
| 7. Sorbitol sodium sulfate | 2.0 |
| 8. Sodium chondroitin sulfate | 1.0 |
| 9. Sodium hyaluronate | 0.5 |
| 10. Propylene glycol | 3.0 |
| 11. Preservative | 1.5 |
| 12. Vitamin E acetate | 0.1 |
| 13. Antioxidant | Suitable amount |
| 14. Perfume | Suitable amount |
| 15. Purified water | Remainder |

*KF-6026 (Shin-Etsu Chemical Co., Ltd.)

(Manufacturing Method)

A: Components 1–6 and 11–12 were mixed with heating.

B: Components 7–10 and 15 were dissolved with heating.

C: B was gradually added to A with stirring, emulsified, cooled, and Component 14 was added. A hair cream was thereby obtained.

The hair cream obtained above spread lightly, was non-sticky, non-oily, and moist, fresh and pleasant to use. It had water-resistant, water-repellent and antiperspirant properties, lasted well, showed no change with temperature or time, and was very stable.

Example 11

Eye Wrinkle Cream

| (Component) | (%) |
|---|---|
| 1. Silicone compound of Example 3 | 20.0 |
| 2. Trimethylsiloxy silicate | 5.0 |
| 3. Polyether oleyl co-modified silicone* | 5.0 |
| 4. Sodium chondroitin sulfate | 2.0 |
| 5. Sodium lactate | 1.0 |
| 6. Glycerin | 50.0 |
| 7. Preservative | Suitable amount |
| 8. Antioxidant | Suitable amount |
| 9. Perfume | Suitable amount |
| 10. Purified water | Remainder |

*KF-6026 (Shin-Etsu Chemical Co., Ltd.)

(Manufacturing Method)

A: Components 1–3 and 8 were mixed with heating.

B: Components 4–7 and 10 were dissolved with heating.

C: B was gradually added to A with stirring, emulsified, cooled, and Component 9 was added. An eye wrinkle cream was thereby obtained.

The eye wrinkle cream obtained above spread lightly, was non-sticky, non-oily, and moist, fresh and pleasant to use. It lasted well, showed no change with temperature or time, and was very stable.

Example 12

Cream

| (Component) | (%) |
|---|---|
| 1. Silicone compound of Example 4 | 20.0 |
| 2. Trioctanoic acid glyceryl | 10.0 |
| 3. Polyether oleyl co-modified silicone* | 4.0 |
| 4. Phenyldimethylstearyl ammonium chloride | 1.0 |
| 5. Dipropylene glycol | 10.0 |
| 6. Maltitol | 10.0 |
| 7. Saponite | 1.5 |
| 8. Preservative | Suitable amount |
| 9. Perfume | Suitable amount |
| 10. Purified water | Remainder |

*KF-6026 (Shin-Etsu Chemical Co., Ltd.)

(Manufacturing Method)

A: Components 1–4 and 8 were mixed with heating.

B: Components 5–7 and 10 were dissolved with heating.

C: B was gradually added to A with stirring, emulsified, cooled, and Component 9 was added. A cream was thereby obtained.

The cream obtained above spread lightly, was non-sticky, non-oily, and moist, fresh and pleasant to use. It had good water-resistant and water-repellent properties, lasted well, showed no change with temperature or time, and was very stable.

Example 13

Hand Cream

| (Component) | (%) |
|---|---|
| 1. Silicone compound of Example 1 | 12.0 |
| 2. Liquid paraffin | 10.0 |
| 3. Organosilicone resin* | 5.0 |
| 4. Polyether oleyl co-modified silicone** | 4.0 |
| 5. Distearyldimethyl ammonium chloride | 0.8 |
| 6. Vitamin E acetate | 0.1 |
| 7. Polyethylene glycol 4000 | 1.0 |
| 8. Glycerin | 10.0 |
| 9. Smectite | 1.2 |
| 10. Preservative | Suitable amount |
| 11. Perfume | Suitable amount |
| 12. Purified water | Remainder |

*Organosilicone resin: average formula is $(CH_3)_{1.60}SiO_{1.20}$, molecular weight is 3,000
**KF-6026 (Shin-Etsu Chemical Co., Ltd.)

(Manufacturing Method)

A: Components 1–6 and 10 were mixed with heating.

B: Components 7–9 and 12 were dissolved with heating.

C: B was gradually added to A with stirring, emulsified, cooled, and Component 11 was added. A handcream was thereby obtained The hand cream obtained above spread lightly, was non-sticky, non-oily, and moist, fresh and pleasant to use. It had good water-resistant and water-repellent properties, lasted well, showed no change with temperature or time, and was very stable.

Example 14

Sunscreen Cream

| (Component) | (%) |
|---|---|
| 1. Silicone compound of Example 2 | 20.0 |
| 2. Liquid paraffin | 10.0 |
| 3. Polyether oleyl co-modified silicone* | 4.0 |
| 4. 4-t-butyl-4'-methoxydibenzoylmethane | 7.0 |
| 5. Distearyldimethyl ammonium chloride | 0.8 |
| 6. Vitamin E acetate | 0.1 |
| 7. Ethanol | 1.0 |
| 8. Smectite | 1.2 |
| 9. Preservative | Suitable amount |
| 10. Perfume | Suitable amount |
| 11. Purified water | Remainder |

*KF-6026 (Shin-Etsu Chemical Co., Ltd.)

(Manufacturing Method)

A: Components 1–6 and 9 were mixed with heating.

B: Components 7, 8 and 11 were heated, and dispersed homogeneously.

C: B was gradually added to A with stirring, emulsified, cooled, and Component 11 was added. A sunscreen cream was thereby obtained.

The sunscreen cream obtained above had a fine texture, spread lightly, was moist, fresh and pleasant, and as it was non-sticky, sand did not stick to it and this made it exceedingly useful.

As a cosmetic product it lasted very well, and gave continuous ultraviolet light protection. It showed no change with temperature or time, and was very stable.

Example 15

Cream

| (Component) | (%) |
| --- | --- |
| 1. Silicone compound of Example 3 | 10.0 |
| 2. Dimethylpolysiloxane (6 cs) | 5.0 |
| 3. Liquid paraffin | 5.0 |
| 4. Polyether oleyl co-modified silicone* | 5.0 |
| 5. Sodium citrate | 2.0 |
| 6. 1,3-butylene glycol | 5.0 |
| 7. Preservative | Suitable amount |
| 8. Perfume | Suitable amount |
| 9. Purified water | Remainder |

*KF-6026 (Shin-Etsu Chemical Co., Ltd.)

(Manufacturing Method)

A: Components 1–4 were mixed with heating.

B: Components 5–7 and 9 were dissolved with heating.

C: B was gradually added to A with stirring, emulsified, cooled, and Component 8 was added. A cream was thereby obtained The cream obtained above spread lightly, was non-sticky, non-oily, and moist, fresh and pleasant to use. It had good water-resistant and water-repellent properties, lasted well, showed no change with temperature or time, and was very stable.

Example 16

Eye Shadow

| (Component) | (%) |
| --- | --- |
| 1. Silicone compound of Example 4 | 15.0 |
| 2. Dimethylpolysiloxane (6 cs) | 10.0 |
| 3. Polyether-modified silicone* | 2.0 |
| 4. PEG (10) lauryl ether | 0.5 |
| 5. Siliconized chromium oxide** | 6.2 |
| 6. Siliconized ultramarine** | 4.0 |
| 7. Siliconized titanium-clad mica* | 6.0 |
| 8. Sodium chloride | 2.0 |
| 9. Propylene glycol | 8.0 |
| 10. Preservative | Suitable amount |
| 11. Perfume | Suitable amount |
| 12. Purified water | Remainder |

*KF-6012 (Shin-Etsu Chemical Co., Ltd.)
**Siliconizing: 3% methylhydrogenpolysiloxane was added to the powder, and heat-treated.

(Manufacturing Method)

A: Components 1–4 were mixed, Components 5–7 were added, and dispersed homogeneously.

B: Components 8–10 and 12 were dissolved homogeneously.

C: B was gradually added to A with stirring, emulsified, cooled, and Component 11 was added. An eye shadow was thereby obtained The eye shadow obtained above spread lightly, was not oily or powdery, and was fresh and pleasant to use.

It had good water-resistant, water-repellent and antiperspirant properties, did not easily deteriorate in cosmetics, showed no change with temperature or time, and was very stable.

Example 17

Eyeliner

| (Component) | (%) |
| --- | --- |
| 1. Silicone compound of Example 1 | 22.0 |
| 2. Dimethylpolysiloxane (6 cs) | 5.0 |
| 3. Jojoba oil | 2.0 |
| 4. Polyether-modified silicone* | 1.0 |
| 5. Siliconized black iron oxide** | 20.0 |
| 6. Ethanol | 5.0 |
| 7. Preservative | Suitable amount |
| 8. Purified water | Remainder |

*KF-6017 (Shin-Etsu Chemical Co., Ltd.)
**Siliconized black iron oxide: 2% methylhydrogenpolysiloxane was added to black iron oxide, and heat-treated.

(Manufacturing Method)

A: Components 1–4 were mixed with heating, Component 5 was added, and dispersed homogeneously.

B: Components 6–8 were dissolved with heating.

C: B was gradually added to A with stirring, and emulsified. An eyeliner was thereby obtained.

The eyeliner obtained above spread lightly, was not oily or powdery, and was fresh and pleasant to use.

It had good water-resistant, water-repellent and antiperspirant properties, did not easily deteriorate in cosmetics, showed no change with temperature or time, and was very stable.

Example 18

Lip Cream

| (Component) | (%) |
| --- | --- |
| 1. Silicone compound of Example 2 | 40.0 |
| 2. Isoparaffin (boiling point 155° C.) | 10.0 |
| 3. Squalane | 10.0 |
| 4. Lanolin | 2.0 |
| 5. Trimethylsiloxysilicate | 3.0 |
| 6. Microcrystalline wax | 3.0 |
| 7. Polyether-modified silicone* | 3.0 |
| 8. Lauroyl glutamic acid dibutyl amide | 5.0 |
| 9. Sodium lactate | 0.3 |
| 10. L-sodium glutamate | 0.3 |
| 11. Sodium hyaluronate | 0.1 |
| 12. Sorbitol | 0.5 |
| 13. Glycerin | 5.0 |
| 14. Red 202 | Suitable amount |
| 15. Menthol | Suitable amount |
| 16. Preservative | Suitable amount |
| 17. Perfume | Suitable amount |
| 18. Purified water | Remainder |

*KF-6017 (Shin-Etsu Chemical Co., Ltd.)

(Manufacturing Method)

A: Components 1–8 were mixed with heating.

B: Components 9–16 and 18 were dissolved with heating.

C: B was gradually added to A with stirring, emulsified, Component 17 was added, and a capsule was filled with the product. A lip cream was thereby obtained.

The solid water-in-oil type lip cream obtained above spread lightly, was not oily, and was moist, fresh and pleasant to use. It lasted well in cosmetics, had a good treatment effect, showed no change with temperature or time, and was very stable.

Example 19

Liquid Emulsion Foundation

| (Component) | (%) |
| --- | --- |
| 1. Dimethylpolysiloxane (6 cs) | 5.0 |
| 2. Silicone compound of Example 3 | 15.0 |
| 3. Squalane | 4.0 |
| 4. Dioctanoic acid neopentyl glycol | 3.0 |
| 5. Myristic acid isostearic acid diglyceride | 2.0 |
| 6. α-monoisostearyl glyceryl ether | 1.0 |
| 7. Polyether-modified silicone* | 1.0 |
| 8. Aluminum distearate | 0.2 |
| 9. Hydrophobically-treated titania** | 5.0 |
| 10. Hydrophobically-treated sericite** | 2.0 |
| 11. Hydrophobically-treated talc** | 3.0 |
| 12. Hydrophobically-treated red ocher** | 0.4 |
| 13. Hydrophobically-treated yellow iron oxide** | 0.7 |
| 14. Hydrophobically-treated black iron oxide** | 0.1 |
| 15. Magnesium sulfate | 0.7 |
| 16. Glycerin | 3.0 |
| 17. Preservative | Suitable amount |
| 18. Perfume | Suitable amount |
| 19. Purified water | Remainder |

*KF-6015 (Shin-Etsu Chemical Co., Ltd.)
**Hydrophobically-treated powder: The powder was treated with 2% stearic acid.

(Manufacturing Method)

A: Components 1–8 were mixed with heating, Components 9–14 were added, and the mixture was rendered homogeneous.

B: Components 15–17 and 19 were dissolved with heating.

C: B was gradually added to A with stirring, emulsified, cooled, and Component 18 was added. A liquid emulsion foundation was thereby obtained.

The liquid emulsion foundation obtained above had a low viscosity and a fine texture, and spread lightly. It was non-sticky, non-oily, and moist, fresh and pleasant to use. It lasted well in cosmetics, showed no change with temperature or time, and was very stable.

Example 20

Antiperspirant

| (Component) | (%) |
| --- | --- |
| 1. Silicone compound of Example 4 | 30.0 |
| 2. Polyether oleyl co-modified silicone* | 1.0 |
| 3. Monooleic acid polyoxyethylene sorbitan (20E.O.) | 0.5 |
| 4. Glycine salt of aluminium-zirconium tetrachloride hydrate | 20.0 |
| 5. Purified water | Remainng amount |

*KF-6026 (Shin-Etsu Chemical Co. Ltd.)

(Manufacturing Method)

A: Components 1–2 were mixed.

B: Component 4 is dissolved in 5, and Component 3 was added.

C: The antiperspirant obtained above spread lightly, was non-sticky and non-oily, did not become over-white, and was pleasant to use. It showed no change with temperature or time, and was very stable.

Example 21

Transparent Gel Cosmetic

| (Component) | (%) |
| --- | --- |
| 1. Silicone compound of Example 1 | 10.0 |
| 2. Polyether-modified silicone* | 10.0 |
| 3. 1,3-butylene glycol | 10.0 |
| 4. Polyethylene glycol 400 | 9.0 |
| 5. 2-hydroxyoctanoic acid | 1.0 |
| 6. Sorbitol (70% aqueous solution) | 10.0 |
| 7. Citric acid | Suitable amount |
| 8. Sodium citrate | Suitable amount |
| 9. Preservative | Suitable amount |
| 10. Perfume | Suitable amount |
| 11. Purified water | Remainder |

*KF-615A (Shin-Etsu Chemical Co., Ltd.)

(Manufacturing Method)

A: Components 3–11 were dissolved homogeneously.

B: Components 1–2 were mixed, and rendered homogeneous.

C: B was gradually added to A with stirring, and emulsified. A transparent gel cosmetic was thereby obtained.

The transparent gel cosmetic obtained above spread lightly, was non-sticky, non-oily, and moist, fresh and pleasant to use. It adapted well to the skin, showed no change with temperature or time, and was very stable.

Example 22

Sunscreen Toilet Water

| (Component) | (%) |
| --- | --- |
| 1. Silicone compound of Example 2 | 14.0 |
| 2. Polyether-modified silicone* | 10.0 |
| 3. Squalane | 1.5 |
| 4. Octyl p-methoxybenzalacetate | 3.0 |
| 5. Hydrophobically-treated ultrafine particle titania** | 2.0 |
| 6. 1,3-butylene glycol | 10.0 |
| 7. Sodium chloride | 2.0 |
| 8. L-proline | 0.1 |
| 9. 2-hydroxyoctanoic acid | 1.0 |
| 10. 2-hydroxypropane acid | 5.0 |
| 11. Sodium hydroxide | Suitable amount |
| 12. Preservative | Suitable amount |
| 13. Perfume | Suitable amount |
| 14. Purified water | Remainder |

*KF-615A (Shin-Etsu Chemical Co., Ltd.)
**Hydrophobically-treated ultrafine particle titania: Titanium TTO-S2 (Sakai Chemical Co. Ltd.)

(Manufacturing Method)

A: Components 6–14 were dissolved homogeneously.

B: Components 1–4 were mixed, Component 5 was added, and the mixture rendered homogeneous.

C: B was gradually added to A with stirring, and emulsified. A sunscreen toilet water was thereby obtained.

The sunscreen toilet water obtained above spread lightly, was non-sticky, non-oily, and moist, fresh and pleasant to use.

It adapted easily to the skin, had an excellent sunscreen effect, showed no change with temperature or time, and was very stable.

Example 23

Cream

| (Component) | (%) |
|---|---|
| 1. Silicone compound of Example 3 | 20.0 |
| 2. Liquid paraffin | 5.0 |
| 3. Polyether-modified silicone* | 1.0 |
| 4. L-ascorbic acid magnesium phosphate | 3.0 |
| 5. Dipropylene glycol | 5.0 |
| 6. Glycerin | 5.0 |
| 7. Preservative | Suitable amount |
| 8. Perfume | Suitable amount |
| 9. Purified water | Remainder |

*KF-615A (Shin-Etsu Chemical Co., Ltd.)

(Manufacturing Method)

A: Components 1–3 uniformity.

B: Components 5–7 were warmed, and rendered homogeneous.

C: Components 4, 9 were dissolved homogeneously.

D: B was gradually added to A with stirring, C was added, emulsified, and Component 8 was added.

A cream was thereby obtained.

The cream obtained above had a fine texture and spread lightly. It was non-sticky, non-oily, and moist, fresh and pleasant to use. It adapted easily to the skin, had excellent beautifying and whitening properties, showed no change with temperature or time, and was very stable.

Example 24

Milky Lotion

| (Component) | (%) |
|---|---|
| 1. Silicone compound of Example 4 | 18.0 |
| 2. Dimethylpolysiloxane (6 cs) | 6.0 |
| 3. Squalane | 5.0 |
| 4. Dioctanoic acid neopentyl glycol | 3.0 |
| 5. α-monooleyl glyceryl ether | 1.0 |
| 6. Polyether-modified silicone* | 2.0 |
| 7. Aluminum distearate | 0.2 |
| 8. Magnesium sulfate | 0.7 |
| 9. Glycerin | 5.0 |
| 10. Preservative | Suitable amount |
| 11. Perfume | Suitable amount |
| 12. Purified water | Remainder |

*KF-6017 (Shin-Etsu Chemical Co., Ltd.)

(Manufacturing Method)

A: Components 1–7 were mixed with heating.

B: Components 8–10 and 12 were dissolved with heating.

C: B was gradually added to A with stirring, emulsified, and Component 11 was added.

A milky lotion was thereby obtained.

The milky lotion obtained above had a low viscosity, and fine texture. It spread lightly, was non-sticky, non-oily, and moist, fresh and pleasant to use. It lasted very well in cosmetics, showed no change with temperature or time, and was very stable.

Example 25

Milky Lotion

| (Component) | (%) |
|---|---|
| 1. Silicone compound of Example 1 | 15.0 |
| 2. Dimethylpolysiloxane (6 cs) | 6.0 |
| 3. Squalane | 5.0 |
| 4. Dioctanoic acid neopentyl glycol | 3.0 |
| 5. α-monooleyl glyceryl ether | 1.0 |
| 6. Polyether oleyl co-modified silicone* | 1.5 |
| 7. Polyether-modified silicone** | 1.0 |
| 8. Aluminum distearate | 0.2 |
| 9. Dextrin fatty acid ester | 1.0 |
| 10. Magnesium sulfate | 0.7 |
| 11. Glycerin | 5.0 |
| 12. Preservative | Suitable amount |
| 13. Perfume | Suitable amount |
| 14. Purified water | Remainder |

*KF6026 (Shin-Etsu Chemical Co. Ltd.)
**KF-6017 (Shin-Etsu Chemical Co., Ltd.)

(Manufacturing Method)

A: Components 1–9 were mixed with heating.

B: Components 10–12 and 14 were dissolved.

C: B was gradually added to A with stirring, emulsified, cooled, and Component 13 was added.

A milky lotion was thereby obtained.

The milky lotion obtained above had a low viscosity and fine texture. It spread lightly, was non-sticky, non-oily, and moist, fresh and pleasant to use. It lasted very well in cosmetics, showed no change with temperature or time, and was very stable.

Example 26

Sunscreen Cream

| (Component) | (%) |
|---|---|
| 1. Silicone compound of Example 2 | 18.0 |
| 2. Methylphenyl polysiloxane | 2.0 |
| 3. Liquid paraffin | 1.5 |
| 4. Polyether-modified silicone* | 4.0 |
| 5. p-methoxy benzalacetic acid octyl | 5.0 |
| 6. 1,3- butylene glycol | 4.0 |
| 7. Sodium chloride | 1.0 |
| 8. Preservative | Suitable amount |
| 9. Perfume | Suitable amount |
| 10. Purified water | Remainder |

*KF-6012 (Shin-Etsu Chemical Co., Ltd.)

(Manufacturing Method)

A: Components 1–5 were mixed with heating.

B: Components 6–8 and 10 were dissolved.

C: B was gradually added to A with stirring, cooled, and Component 9 was added.

A sunscreen cream was thereby obtained.

The sunscreen cream obtained above had a fine texture, and spread lightly. It was moist and fresh, non-oily, non-sticky, and very easy to use. It had excellent water-resistant and antiperspirant properties, lasted well in cosmetics, gave continuous ultraviolet light protection, showed no change with temperature or time, and was very stable.

Example 27

Cream

| (Component) | (%) |
| --- | --- |
| 1. Silicone compound of Example 3 | 20.0 |
| 2. Methylphenyl polysiloxane | 5.0 |
| 3. Polyether-modified silicone* | 1.0 |
| 4. Dextrin fatty acid ester | 1.0 |
| 5. Glycerin | 5.0 |
| 6. Sodium chloride | 1.0 |
| 7. Preservative | Suitable amount |
| 8. Perfume | Suitable amount |
| 9. Purified water | Remainder |

*KF-6012 (Shin-Etsu Chemical Co., Ltd.)

(Manufacturing Method)

A: Components 1–4 were mixed with heating.

B: Components 5–7 and 9 were dissolved.

C: B was gradually added to A with stirring, cooled, and Component 8 was added.

A cream was thereby obtained.

The cream obtained above had a fine texture, and spread lightly. It was moist and fresh, non-oily, non- sticky, and very easy to use. It had excellent water-resistant and antiperspirant properties, lasted well in cosmetics, gave continuous ultraviolet light protection, showed no change with temperature or time, and was very stable.

Example 28

Foundation

| (Component) | (%) |
| --- | --- |
| 1. Silicone compound of Example 4 | 18.0 |
| 2. Methylphenyl polysiloxane | 5.0 |
| 3. Monoisostearic acid sorbitan | 0.5 |
| 4. Monoisostearic acid diglyceryl | 0.5 |
| 5. Polyether-modified silicone* | 1.0 |
| 6. Octyl p-methoxycinnamate | 3.0 |
| 7. Titania | 10.0 |
| 8. Red ocher | 0.13 |
| 9. Yellow iron oxide | 0.3 |
| 10. Black iron oxide | 0.07 |
| 11. Talc | 2.5 |
| 12. Sorbitol | 2.0 |
| 13. Magnesium sulfate | 0.1 |
| 14. Ethanol | 10.0 |
| 15. Preservative | Suitable amount |
| 16. Perfume | Suitable amount |
| 17. Purified water | Remainder |

*KF-6012 (Shin-Etsu Chemical Co., Ltd.)

(Manufacturing Method)

A: Components 7–11 were mixed homogeneously.

B: Components 1–6 and 15 were mixed with heating, A was added, and dispersed homogeneously.

C: Components 12–13 and 17 were warmed, B was added, emulsified and cooled, and Components 14 and 16 were added. A foundation was thus obtained.

The foundation obtained above was non-sticky, spread lightly, and had a very pleasant, cool feel.

Its emulsion state was good, and it was not much affected by temperature. It did not separate or lump together with time, and was very stable.

Example 29

Liquid Foundation

| (Component) | (%) |
| --- | --- |
| 1. Silicone compound of Example 1 | 15.0 |
| 2. Dimethylpolysiloxane (6 cs) | 5.0 |
| 3. Liquid paraffin | 3.0 |
| 4. Polyether-modified silicone* | 3.0 |
| 5. Palmitic acid | 0.5 |
| 6. Hydrophobically-treated silica** | 5.0 |
| 7. Titania | 6.0 |
| 8. Red ocher | 0.25 |
| 9. Yellow iron oxide | 0.6 |
| 10. Black iron oxide | 0.12 |
| 11. Sericite | 8.03 |
| 12. Dipropylene glycol | 10.0 |
| 13. Magnesium sulfate | 2.0 |
| 14. Preservative | Suitable amount |
| 15. Antioxidant | Suitable amount |
| 16. Perfume | Suitable amount |
| 17. Purified water | Remainder |

*KF6015 (Shin-Etsu Chemical Co., Ltd.)
**Hydrophobically-treated silica: Aerogel RY200 (Japan Aerogel Co., Ltd.)

(Manufacturing Method)

A: Components 8–12 were mixed homogeneously.

B: Components 1–7 and 16 were heated to 70 degrees, and mixed, A was added, and dispersed homogeneously.

C: Components 13–18 were heated to 70 degrees, B was added, emulsified and cooled, and Component 17 was added. A liquid foundation was thus obtained.

The foundation obtained above was non-sticky, spread lightly, and had a very pleasant, cool feel.

Its emulsion state was good, it lasted very well in cosmetics, and it was not much affected by temperature. It was very stable over time.

Example 30

Sunscreen Lotion

| (Component) | (%) |
| --- | --- |
| 1. Silicone compound of Example 2 | 25.0 |
| 2. Monoisostearic acid diglyceryl | 1.5 |
| 3. Pentaisostearic acid decaglyceryl | 1.5 |
| 4. Polyether-modified silicone* | 0.5 |
| 5. Olive oil | 1.0 |
| 6. Particulate titania | 7.0 |
| 7. Glycerin | 5.0 |
| 8. Sodium chloride | 1.5 |
| 9. Preservative | Suitable amount |
| 10. Perfume | Suitable amount |
| 11. Purified water | Remainder |

*KF-6012 (Shin-Etsu Chemical Co., Ltd.)

(Manufacturing Method)

A: Components 1–5 were mixed with heating, and Component 6 was homogeneously dispersed.

B: Components 7–9 and 11 were mixed with heating.

C: B was gradually added to A with stirring, emulsified, cooled, and Component 10 was added.

A sunscreen lotion was thereby obtained.

The sunscreen lotion obtained above had a low viscosity, and a fine texture. It spread lightly, was non-sticky, and moist and fresh. It lasted very well in cosmetics and was able to give continuous ultraviolet light protection. It showed no change with temperature or time, and had excellent powder dispersion stability and emulsion stability.

Example 31

Sunscreen Lotion

| (Component) | (%) |
|---|---|
| 1. Silicone compound of Example 3 | 20.0 |
| 2. Methylphenyl polysiloxane | 3.0 |
| 3. Monoisostearic acid sorbitan | 1.0 |
| 4. Polyether-modified silicone* | 0.5 |
| 5. Trimethylsiloxysilicic acid | 1.0 |
| 6. p-methoxycinnamic acid octyl | 4.0 |
| 7. Particulate titania | 8.0 |
| 8. Sorbitol | 2.0 |
| 9. Sodium chloride | 2.0 |
| 10. Preservative | Suitable amount |
| 11. Perfume | Suitable amount |
| 12. Purified water | Remainder |

*KF-6012 (Shin-Etsu Chemical Co., Ltd.)

(Manufacturing Method)

A: Components 1–6 were mixed with heating, and Component 7 was dispersed homogeneously.

B: Components 8–10 and 12 were mixed with heating.

C: B was gradually added to A with stirring, emulsified, cooled, and Component 11 was added.

A sunscreen lotion was thereby obtained.

The sunscreen lotion obtained above had a fine texture, spread lightly, was non-sticky, and moist and fresh. It lasted very well in cosmetics, and was able to give continuous ultraviolet light protection. It showed no change with temperature or time, and was exceedingly stable.

Example 32

Beautifying Lotion

| (Component) | (%) |
|---|---|
| 1. Silicone compound of Example 4 | 12.0 |
| 2. Triisooctanoic acid glyceryl | 10.0 |
| 3. Polyether-modified silicone* | 2.0 |
| 4. Silicone gel** | 0.2 |
| 5. Glycerin | 10.0 |
| 6. Ascorbic acid magnesium phosphate | 3.0 |
| 7. Sodium chloride | 2.0 |
| 8. Preservative | Suitable amount |
| 9. Perfume | Suitable amount |
| 10. Purified water | Remainder |

*KF6017 (Shin-Etsu Chemical Co., Ltd.)
**Silicone gel: KSG21 (Shin-Etsu Chemical Co., Ltd.)

(Manufacturing Method)

A: Components 1–4 were mixed with heating.

B: Component 5–8 and 10 were heated, and dissolved homogeneously.

C: B was gradually added to A with stirring, emulsified, cooled, and Component 9 was added.

A beautifying lotion was thereby obtained.

The beautifying lotion obtained above had a fine texture, spread lightly, was non-sticky, and moist and fresh. It showed no change with temperature or time, and was exceedingly stable.

Example 33

Cream

| (Component) | (%) |
|---|---|
| 1. Silicone compound of Example 1 | 18.0 |
| 2. Dimethylpolysiloxane (100 cs) | 2.0 |
| 3. Polypropylene glycol (3) myrystyl ether | 0.5 |
| 4. Polyether oleyl co-modified silicone* | 2.5 |
| 5. Hydrophobically-treated particulate titania** | 1.0 |
| 6. Glycerin | 3.0 |
| 7. 70% sorbitol | 5.0 |
| 8. Citric acid | 25.0 |
| 9. Sodium chloride | 0.6 |
| 10. Preservative | Suitable amount |
| 11. Perfume | Proper amount |
| 12. 32% ammonia water | 4.5 |
| 13. Purified water | Remainder |

*KF-6026 (Shin-Etsu Chemical Co., Ltd.)
**Hydrophobically-treated particulate titania: Aluminum stearate-treated particulate titania (Manufacturing Method)

A: Components 1–4 and 11 were mixed, and Component 5 was blended with stirring.

B: Components 6–10 and 12–13 were dissolved homogeneously.

C: B was gradually added to A, and emulsified. A cream was thereby obtained.

Although the cream obtained above contained a large amount of citric acid, it spread lightly when applied, had no tackiness, and was moist and non-sticky even after use. It showed no change with temperature or time, and was exceedingly stable.

Example 34

Aftershave Cream

| (Component) | (%) |
|---|---|
| 1. Silicone compound of Example 2 | 5.0 |
| 2. Polyether oleyl co-modified silicone* | 5.0 |
| 3. Polyethylene glycol (molecular weight: 400) | 5.0 |
| 4. L-sodium glutamate | 2.0 |
| 5. Allantoin | 0.1 |
| 6. Aloe extract | Suitable amount |
| 7. Preservative | Suitable amount |
| 8. Antioxidant | Suitable amount |
| 9. Perfume | Suitable amount |
| 10. Purified water | Remainder |

*KF-6026 (Shin-Etsu Chemical Co., Ltd.)

(Manufacturing Method)

A: Components 1–3 and 9,10 were mixed with heating.

B: Components 4–8 were mixed with heating.

C: B was gradually added to A, and emulsified. An aftershave cream was thereby obtained.

The aftershave cream obtained above had a high viscosity, and did not drip. It spread lightly when applied and was non-sticky. After application, it was light but very moist, and very easy to use. It was also exceedingly stable.

Example 35

Deodorant

| (Component) | (%) |
| --- | --- |
| 1. Silicone compound of Example 3 | 12.0 |
| 2. Dimethylpolysioxane (6 cs) | 4.0 |
| 3. Polyether-modified silicone* | 1.0 |
| 4. Propylene glycol | 31.0 |
| 5. Triclosan | 0.1 |
| 6. Glycerin | 15.0 |
| 7. Preservative | Suitable amount |
| 8. Perfume | Suitable amount |
| 9. Purified water | Remainder |

*F-615A (Shin-Etsu Chemical Co., Ltd.)

(Manufacturing Method)

A: Components 1–3 were mixed.

B: Component 5 was dissolved in 4, and Components 6–9 were mixed.

C: A was stirred vigorously, B was added, and emulsified.

D: 65 parts of the product and 35 parts of an injection agent (n- butane, isobutane, propane mixture) were added to an aerosol can. A deodorant was thereby obtained.

The deodorant obtained above did not drip even when employed at high concentration, was non-sticky and light. It continued to have an effect over time, and was very easy to use.

Example 36

Liquid Foundation

| (Component) | (%) |
| --- | --- |
| 1. Silicone compound of Example 4 | 16.0 |
| 2. Dimethylpolysiloxane (6 cs) | 8.0 |
| 3. p-methoxybenzalacetic acid octyl | 3.0 |
| 4. 12-hydroxystearic acid | 1.0 |
| 5. Fluorine-modified silicone* | 15.0 |
| 6. Fluorine polyether-modified silicone** | 5.0 |
| 7. Spherical silicone resin powder*** | 3.0 |
| 8. Fluorine compound-treated particulate titania**** | 8.0 |
| 9. Fluorine compound-treated mica titanium**** | 1.0 |
| 10. Fluorine compound-treated titania**** | 5.0 |
| 11. Fluorine compound-treated red ocher**** | 0.9 |
| 12. Fluorine compound-treated yellow iron oxide**** | 2.0 |
| 13. Fluorine compound-treated black iron oxide**** | 1.0 |
| 14. Ethanol | 15.0 |
| 15. Glycerin | 3.0 |
| 16. Magnesium sulfate | 1.0 |
| 17. Preservative | Suitable amount |
| 18. Perfume | Suitable amount |
| 19. Purified water | Remainder |

*FPD-6131 (Shin-Etsu Chemical Co., Ltd.)
**FL-100 (Shin-Etsu Chemical Co., Ltd.)
***KMP590 (Shin-Etsu Chemical Co., Ltd.)
****Fluorine compound-treated: 5% coating by perfluoroalkylethyl phosphoric acid diethanolamine salt:

(Manufacturing Method)

A: Components 7–13 were mixed homogeneously.

B: Components 1–6 were heated to 70° C., mixed, A was added, and dispersed homogeneously.

C: Components 14–17 and 19 were warmed to 40° C., B was added gradually, emulsified, cooled, and Component 18 was added. A liquid foundation was thereby obtained.

The liquid foundation obtained above was non-sticky, spread lightly, and had a very pleasant, cool feel.

It showed no change with temperature or time, and was exceedingly stable.

Example 37

Milky Lotion

| (Component) | (%) |
| --- | --- |
| 1. Silicone compound of Example 1 | 15.0 |
| 2. Methylphenyl polysiloxane | 5.0 |
| 3. Squalene | 5.0 |
| 4. Tetra-2-ethylhexanoic acid pentaerythritol | 5.0 |
| 5. Polyether-modified silicone* | 3.0 |
| 6. Organopolysioxane elastomer spherical powder** | 2.0 |
| 7. Hydrophobically-treated silica*** | 0.5 |
| 8. Ascorbic acid magnesium phosphate | 1.0 |
| 9. Sodium chloride | 1.0 |
| 10. Polyethylene glycol 11000 | 1.0 |
| 11. Propylene glycol | 8.0 |
| 12. Preservative | Suitable amount |
| 13. Perfume | Suitable amount |
| 14. Purified water | Remainder |

*KF-6017 (Shin-Etsu Chemical Co., Ltd.)
**KMP594 (Shin-Etsu Chemical Co., Ltd.)
***Aerogel R972 (Japan Aerogel Co., Ltd.)

(Manufacturing Method)

A: Components 1–5 were mixed homogeneously, Components 6, 7 were added, and dispersed homogeneously.

B: Components 8–10 were added to Component 14, dissolved, Components 11, 12 were homogenized, and then added.

C: B was gradually added to A, emulsified, cooled, and Component 13 was added. A milky lotion was thereby obtained.

The milky lotion obtained above spread lightly, was light and non-sticky. It showed no change with temperature or time, and was very easy and safe to use.

Example 38

Moisture-Retaining Cream

| (Component) | (%) |
| --- | --- |
| 1. Silicone compound of Example 2 | 10.0 |
| 2. Methylphenyl polysiloxane | 3.0 |
| 3. Liquid paraffin | 5.0 |
| 4. tetra-2-ethylhexanoic acid pentaerythritol | 3.0 |
| 5. 2-ethylhexanoic acid cetyl | 5.0 |
| 6. Polyether-modified silicone* | 1.0 |
| 7. Organopolysiloxane elastomer spherical powder** | 2.5 |
| 8. Hydrophobically-treated silica*** | 2.0 |
| 9. Zinc stearate | 2.0 |
| 10. Vitamin E acetate | 3.0 |
| 11. Polyethylene glycol 400 | 1.0 |
| 12. Sodium lactate | 1.0 |
| 13. 1,3-butylene glycol | 5.0 |

-continued

| (Component) | (%) |
|---|---|
| 14. Preservative | Suitable amount |
| 15. Perfume | Suitable amount |
| 16. Purified water | Remainder |

*KF-6017 (Shin-Etsu Chemical Co., Ltd.)
**KMP594 (Shin-Etsu Chemical Co., Ltd.)
***Aerogel R972 (Japan Aerogel Co., Ltd.)

(Manufacturing Method)

A: Components 1–6 and 9–10 were mixed homogeneously, Components 7, 8 were added, and dispersed homogeneously.

B: Components 11–14 and 16 were added, and dissolved.

C: B was gradually added to A, emulsified, cooled, and Component 15 was added. A moisture-retaining cream was thereby obtained.

The moisture-retaining cream obtained above spread lightly, was fresh, pleasant to use, and non-sticky. It showed no change with temperature or time, and was exceedingly easy to use and stable.

Example 39

Hand Cream

| (Component) | (%) |
|---|---|
| 1. Silicone compound of Example 3 | 30.0 |
| 2. Liquid paraffin | 10.0 |
| 3. Amino-modified silicone gum* | 15.0 |
| 4. Polyether-modified silicone** | 4.0 |
| 5. Distearyl dimethyl ammonium chloride | 0.8 |
| 6. Vitamin E acetate | 0.1 |
| 7. Polyethylene glycol 4000 | 1.0 |
| 8. Glycerin | 10.0 |
| 9. Smectite | 1.2 |
| 10. Preservative | Suitable amount |
| 11. Perfume | Suitable amount |
| 12. Purified water | Remainder |

*Amine equivalent 70000 g/mol
**KF-6017 (Shin-Etsu Chemical Co., Ltd.)

(Manufacturing Method)

A: Components 1, 3 were dissolved with heating, and Components 2, 4–6, 10 were added with heating.

B: Components 7–9 and 12 were mixed with heating.

C: B was gradually added to A, emulsified, cooled, and Component 11 was added. A hand cream was thereby obtained.

The hand cream obtained above was non-sticky, spread lightly, and was pleasant to use. It effectively protected the skin during kitchenwork, and had excellent temperature stability.

Example 40

Eyeliner

| (Component) | (%) |
|---|---|
| 1. Silicone compound of Example 4 | 22.0 |
| 2. Dimethylpolysiloxane (6 cs) | 5.0 |

-continued

| (Component) | (%) |
|---|---|
| 3. Siliconized black iron oxide | 20.0 |
| 4. Vitamin E acetate | 0.2 |
| 5. Jojoba oil | 2.0 |
| 6. Bentonite | 3.0 |
| 7. Polyether-modified silicone* | 2.0 |
| 8. Ethanol | 10.0 |
| 9. 1,3-butylene glycol | 10.0 |
| 10. Preservative | Suitable amount |
| 11. Perfume | Suitable amount |
| 12. Purified water | Remainder |

*KF-6012 (Shin-Etsu Chemical Co., Ltd.)

(Manufacturing Method)

A: Components 1–2, 4–7 were mixed, Component 3 was added, and dispersed homogeneously.

B: Component 8–10 and 12 were mixed.

C: B was gradually added to A, emulsified, cooled, and Component 11 was added. An eyeliner was thereby obtained.

The eyeliner obtained above spread lightly, was easy to draw with, was cool and pleasant to use, and non-sticky. It showed no change with temperature or time, and was exceedingly easy to use and stable.

It also had excellent water resistance properties and antiperspirant properties, and lasted very well in cosmetics.

Example 41

Cream

| (Component) | (%) |
|---|---|
| 1. Silicone compound of Example 1 | 16.0 |
| 2. Dimethylpolysioxane (6 cs) | 4.0 |
| 3. Polyether-modified silicone* | 5.0 |
| 4. POE (5) octyl dodecyl ether | 1.0 |
| 5. Monostearin acid polyoxyethylene sorbitan (20E.O.) | 0.5 |
| 6. Silicic acid anhydride-treated zinc oxide** | 2.0 |
| 7. Siliconized particulate titania | 10.0 |
| 8. Liquid paraffin | 2.0 |
| 9. Macadamia nut oil | 1.0 |
| 10. Scutellaria Root extract*** | 1.0 |
| 11. Gentiana extract**** | 0.5 |
| 12. Ethanol | 5.0 |
| 13. 1,3-butylene glycol | 2.0 |
| 14. Preservative | Suitable amount |
| 15. Perfume | Suitable amount |
| 16. Purified water | Remainder |

*KF-6012 (Shin-Etsu Chemical Co., Ltd.)
**Silicic acid anhydride-treated zinc oxide: Silica of particle size 0.01–10 micrometers containing 50% zinc oxide: Sunsphere SZ-5 (Asahi Glass Co., Ltd.)
***Ogon extract: extract with 50% 1,3-butylene glycol water
****Gentiana extract: extract with 20% ethanol water.

(Manufacturing Method)

A: Components 6–9 were mixed homogeneously, and dispersed.

B: Components 1–5 were mixed, and A was added.

C: Components 10–14 and 16 were mixed, B was added, and emulsified.

D: C was cooled, and Component 15 was added. A cream was thereby obtained.

The cream obtained above was non-sticky, and spread lightly. It also had excellent skin feel and adhesion, a lustrous finish, and lasted exceedingly well in cosmetics. It showed no change with temperature or time, and was exceedingly stable.

Example 42

Foundation

| (Component) | (%) |
|---|---|
| 1. Silicone compound of Example 2 | 27.0 |
| 2. Methylphenyl polysiloxane | 3.0 |
| 3. Triisooctanoic acid glyceryl | 10.0 |
| 4. Polyether oleyl co-modified silicone* | 1.0 |
| 5. Mono isostearic acid polyglyceryl | 3.0 |
| 6. Hydrophobically-treated mixed powder (Note 1) | 18.0 |
| 7. Red ocher | 1.2 |
| 7. Yellow iron oxide | 2.6 |
| 8. Black iron oxide | 0.2 |
| 9. 1,3-butylene glycol | 7.0 |
| 10. Sodium chloride | 0.5 |
| 11. Preservative | Suitable amount |
| 12. Perfume | Suitable amount |
| 13. Purified water | Remainder |
| (Note 1) | |
| Hydrophobically-treated mixed powder | |
| a. Particulate titania | 8.0 |
| b. Particulate zinc oxide | 4.0 |
| c. Talc | 3.0 |
| d. Mica | 3.0 |

*KF-6026 (Shin-Etsu Chemical Co., Ltd.)

(Manufacturing Method)

A: Components a . . . d were mixed, 1% methylhydrogen polysiloxane was added to the powder, and the product was heat-treated.

B: Components 1–5 were mixed, dissolved with warming, and Components 6–9 were dispersed homogeneously.

C: Components 10–12 and 14 were mixed, B was added, and emulsified.

D: C was cooled, and Component 13 was added. A foundation was thereby obtained.

The foundation obtained above was non-sticky, and spread lightly. It also had excellent skin feel and adhesion, a lustrous finish, and lasted exceedingly well in cosmetics. It showed no change with temperature or time, and was exceedingly stable.

Example 43

Suncut Cream

| (Component) | (%) |
|---|---|
| 1. Silicone compound of Example 3 | 17.5 |
| 2. KP545* | 12.0 |
| 3. Triisooctanoic acid glyceryl | 5.0 |
| 4. Octyl p-methoxycinnamate | 6.0 |
| 5. KSG21** | 5.0 |
| 6. Polyether oleyl co-modified silicone*** | 1.0 |
| 7. Lipophilic-treated zinc oxide | 20.0 |
| 8. Sodium chloride | 0.5 |
| 9. 1,3-butylene glycol | 2.0 |

-continued

| (Component) | (%) |
|---|---|
| 10. Preservative | Suitable amount |
| 11. Perfume | Suitable amount |
| 12. Purified water | Remainder |

*KP545: Acryl silicone resin /50%-D5 solution (Shin-Etsu Chemical Co., Ltd.)
**KSG21: Silicone gel (Shin-Etsu Chemical Co., Ltd.)
***KF-6026 (Shin-Etsu Chemical Co., Ltd.)

(Manufacturing Method)

A: Component 2 was added to part of Component 1, homogenized, Component 7 was added, and dispersed by a bead mil.

B: The remainder of Component 1 and Components 3–6 were mixed, and rendered homogeneous.

C: Components 8–10 and 12 were mixed and dissolved.

D: C was added to B, emulsified, A and Component 11 were added, and a suncut cream was thereby obtained.

The suncut cream obtained above was non-sticky, and spread lightly. It also had excellent skin feel and adhesion, a lustrous finish, and lasted exceedingly well in cosmetics. It was very stable to temperature or time.

Example 44

O/W Hand Cream

| (Component) | (%) |
|---|---|
| 1. Silicone compound of Example 4 | 10.0 |
| 2. KSG16* | 2.0 |
| 3. Isoparaffin | 5.0 |
| 4. Vaseline | 5.0 |
| 5. Triisooctanoic acid glyceryl | 3.0 |
| 6. Polyether-modified silicone** | 0.5 |
| 7. Polyoxyethlene sorbitan monooleate | 1.0 |
| 8. Sepigel 305*** | 2.0 |
| 9. 1,3-butylene glycol | 5.0 |
| 10. Glycerin | 5.0 |
| 11. Preservative | Suitable amount |
| 12. Perfume | Suitable amount |
| 13. Purified water | Remainder |

*KSG16: Silicone gel (Shin-Etsu Chemical Co., Ltd.)
**KF-6017 (Shin-Etsu Chemical Co., Ltd.)
***Sepigel 305 (SEPPIC Co., Ltd.)

(Manufacturing Method)

A: Components 1–7 were mixed homogeneously.

B: Components 8–11 and 13 were mixed homogeneously.

C: B was added to A, emulsified, and Component 12 was added. An O/W hand cream was thereby obtained.

The hand cream obtained above was non-sticky, and spread lightly. It also had excellent skin feel and adhesion, a lustrous finish, and lasted exceedingly well in cosmetics. It showed no change with temperature or time, and was exceedingly stable.

Example 45

O/W Hand Cream

| (Component) | (%) |
|---|---|
| 1. Silicone compound of Example 1 | 10.0 |
| 2. Stearyl-modified acryl silicone | 8.0 |
| 3. Cetanol | 1.0 |
| 4. Triisooctanoic acid glyceryl | 5.0 |
| 5. Stearic acid | 3.0 |
| 6. Monostearic acid glyceryl | 1.5 |
| 7. Polyether-modified silicone* | 0.7 |
| 8. Sesquioleic acid sorbitan | 0.5 |
| 9. Monooleic acid polyoxyethylene sorbitan | 1.0 |
| 10. Sodium hydroxide (1% aqueous solution) | 10.0 |
| 11. 1,3-butylene glycol | 5.0 |
| 12. Preservative | Suitable amount |
| 13. Perfume | Suitable amount |
| 14. Purified water | Remainder |

*KF-6015 (Shin-Etsu Chemical Co., Ltd.)

(Manufacturing Method)

A: Components 1–9 were dissolved with heating.

B: Components 10–12 and 14 were mixed, and heated.

C: B is added to A, emulsified, cooled, and Component 13 was added. An O/W hand cream was thereby obtained.

The hand cream obtained above was non-sticky, and spread lightly. It also had excellent skin feel and adhesion, a lustrous finish, and lasted exceedingly well in cosmetics. It showed no change with temperature or time, and was exceedingly stable.

Example 46

Aerosol Composition

| (Component) | (%) |
|---|---|
| 1. Siliconized mica | 3.0 |
| 2. Chlorohydroxyaluminium | 2.0 |
| 3. Isopropyl methylphenol | 0.3 |
| 4. Sesquioleic acid sorbitan | 0.2 |
| 5. Myristic acid isopropyl | 5.0 |
| 6. Silicone compound of Example 2 | 5.0 |
| 7. Perfume | Suitable amount |
| 8. Injection agent | Remainder |

(Manufacturing Method)

A: Components 1–7 were mixed.

B: An aerosol can was filled with A, and then with Component 8.

The aerosol composition of this invention obtained above had a strong deodorant effect. When it was applied, it was non-sticky and non-heavy, spread lightly, had a light, smooth feel, and as it was easily redispersed, it was exceedingly useful.

INDUSTRIAL FIELD OF THE INVENTION

From the above, it is seen that by blending the silicone composition of this invention, it is possible to provide a cosmetic material which has excellent skin contact, is non-sticky, has an excellent feel and is easy to manufacture. In addition, it showed no change with temperature or time, and was exceedingly stable.

What is claimed is:

1. A silicone compound having a melting point of 40° C. or less represented by the general formula:

$$R^1_a R^2_b SiO_{(4-a-b)/2}$$

wherein:

R$^1$ is, independently, a monofunctional alkyl group, aryl group, aralkyl group or fluorine-substituted alkyl group having 1–10 carbon atoms, which does not contain an aliphatic unsaturated bond, R$^2$ is an organic group represented by the general formula:

$$-(C_pH_{2p})O(C_qH_{2q}O)_r-X, \text{ where:}$$

X is a monofunctional residue of a sterol absent a hydroxyl group, a is a number of the formula:

$1.0 \leq a \leq 2.5$, b is a number of the formula:

$0.00 \leq b \leq 1.0$, where:

$1.5 \leq a+b \leq 2.6$, p, q and r are, independently, integers of the formulae:

$2 \leq p \leq 6$, $2 \leq q \leq 4$, and $3 \leq r \leq 200$.

2. A cosmetic material comprising a silicone compound according to claim 1.

3. A cosmetic material, comprising: (a) 0.1–70 wt % of a silicone compound according to claim 1, and (b) at least one of a phospholipid, a compound having an alcoholic hydroxy group in its molecular structure, an oil, water, a powder, a colorant, a surfactant, a crosslinked organopolysiloxane, a silicone resin or an ultraviolet light protection component.

4. A cosmetic material according to claim 3, wherein the content of the phospholipid is 0.01–10.0 wt %.

5. A cosmetic material according to claim 3, wherein the content of the compound having the alcoholic hydroxy group in its molecular structure is 0.1–70.0 wt %.

6. A cosmetic material according to claim 3, comprising the compound having the alcoholic hydroxy group in its molecular structure, which is a water-soluble polymer.

7. A cosmetic material according to claim 3, wherein the content of the oil is 0.1–50.0 wt %.

8. A cosmetic material according to claim 7, wherein at least part of the oil is a liquid at room temperature.

9. A cosmetic material according to claim 7, wherein at least part of the oil is a silicone oil containing a volatile silicone, or an oil having a repeating unit of —[O—Si]— in its molecular skeleton, and a fluorine group or an amino group.

10. A cosmetic material according to claim 3, comprising the powder or colorant, wherein at least part of the powder or colorant is a powder having a silicone elastomer as its skeleton, or a powder having a repeating unit of —[O—Si]— in its molecular structure.

11. A cosmetic material according to claim 3, comprising the surfactant wherein the surfactant is a modified silicone having a polyoxyalkylene chain in the molecule.

12. A cosmetic material according to claim 3, comprising the surfactant wherein the HLB of the surfactant is 2–18.

13. A cosmetic material according to claim 3, comprising the crosslinked organopolysiloxane wherein the crosslinked organopolysiloxane can absorb at least its own weight of low viscosity silicone of 0.65 mm$_2$sec–100 mm$_2$/sec.

14. A cosmetic material according to claim 3, comprising the crosslinked organopolysiloxane wherein the crosslinked organopolysiloxane is a reaction product of an organohydrogen polysiloxane and a crosslinking agent having two or more vinylic reactive sites in the molecule.

15. A cosmetic material according to claim 3, comprising the crosslinked organopolysiloxane wherein the crosslinked organopolysiloxane contains at least one of a polyoxyalkylene part, an alkyl part, an alkenyl part, an aryl part or a fluoroalkyl part.

16. A cosmetic material according to claim 3, comprising the silicone resin, which is acryl silicone.

17. A cosmetic material according to claim 16, wherein the acryl silicone is an acryl silicone having at least one of a pyrrolidone part, a long-chain alkyl part, a polyoxyalkylene part or a fluoroalkyl part.

18. A cosmetic material according to claim 3, comprising the silicone resin, which is a silicone reticulation compound.

19. A cosmetic material according to claim 18, wherein the silicone reticulation compound is a silicone reticulation compound containing at least one of a pyrrolidone part, a long-chain alkyl part, a polyoxyalkylene part, a fluoroalkyl part or an amino moiety.

20. A cosmetic material according to claim 3, wherein the cosmetic material is a skin care cosmetic material.

21. A cosmetic material according to claim 3, wherein the cosmetic material is a hair treatment cosmetic material.

22. A cosmetic material according to claim 3, wherein the cosmetic material is an antiperspirant.

23. A cosmetic material according to claim 3, wherein the cosmetic material is a make-up cosmetic product.

24. A cosmetic material according to claim 3, wherein the cosmetic material is an ultraviolet protection cosmetic material.

25. A cosmetic material according to claim 2, wherein the material is a milky lotion, cream, solid, paste, gel, powder, laminate, mousse or spray.

26. A silicone compound according to claim 1, wherein the hydroxyl group eliminated from the sterol is from the third, sixteenth or seventeenth position on the sterol.

27. A silicone compound according to claim 1, wherein the sterol is cholesterol, ergosterol, lanosterol, phytosterol, or estradiol.

* * * * *